United States Patent [19]

Watson

[11] 4,230,116
[45] Oct. 28, 1980

[54] TUBAL LIGATION INSTRUMENT WITH ANESTHESIA MEANS

[75] Inventor: Trevor F. Watson, Columbia, Mo.
[73] Assignee: Kli, Inc., Newtown, Pa.
[21] Appl. No.: 947,467
[22] Filed: Oct. 2, 1978
[51] Int. Cl.³ ............................................. A61B 17/12
[52] U.S. Cl. ................................................ 128/303 A
[58] Field of Search ................ 128/303 A, 326, 4, 6, 128/184, 188, 347, 303.1, 303.15, 303.17

[56] References Cited

U.S. PATENT DOCUMENTS

| | | | |
|---|---|---|---|
| 2,131,924 | 10/1938 | Wappler | 128/6 |
| 2,541,542 | 2/1951 | Perez et al. | 128/347 X |
| 4,085,743 | 4/1978 | Yoon | 128/303 A X |

FOREIGN PATENT DOCUMENTS

| | | | |
|---|---|---|---|
| 716726 | 12/1931 | France | 128/347 |
| 934257 | 5/1948 | France | 128/4 |

*Primary Examiner*—Robert W. Michell
*Assistant Examiner*—Michael H. Thaler
*Attorney, Agent, or Firm*—Miller & Prestia

[57] ABSTRACT

The tubal ligation instrument of the present invention includes structure for ligating anatomical tubes within the human or animal body, and structure for anesthetizing the anatomical tubes being ligated. An example of an anatomical tube is a Fallopian tube. The instrument further includes a structure for grasping the anatomical element. The grasping structure extends through a channel in the instrument housing. Usually the grasping structure is a rod having forceps tongs at one end with a flat surface formed on a side portion of the rod. Consequently, the rod does not occupy the entire housing leaving a channel between the rod and the housing. On an outside surface of the instrument housing is an anesthesia receiving means, typically a stopcock. A channel through the stopcock, through which anesthesia may flow, is capable of communicating with the channel between the rod and the housing. The application of anesthesia to an anatomical element is accomplished by introducing the anesthesia through the stopcock and into the unoccupied channel of the housing. Thus, a surgeon directing the end of the instrument to an anatomical element can apply an anesthetic agent to the anatomical element intraabdominally, by the method of the present invention.

17 Claims, 17 Drawing Figures

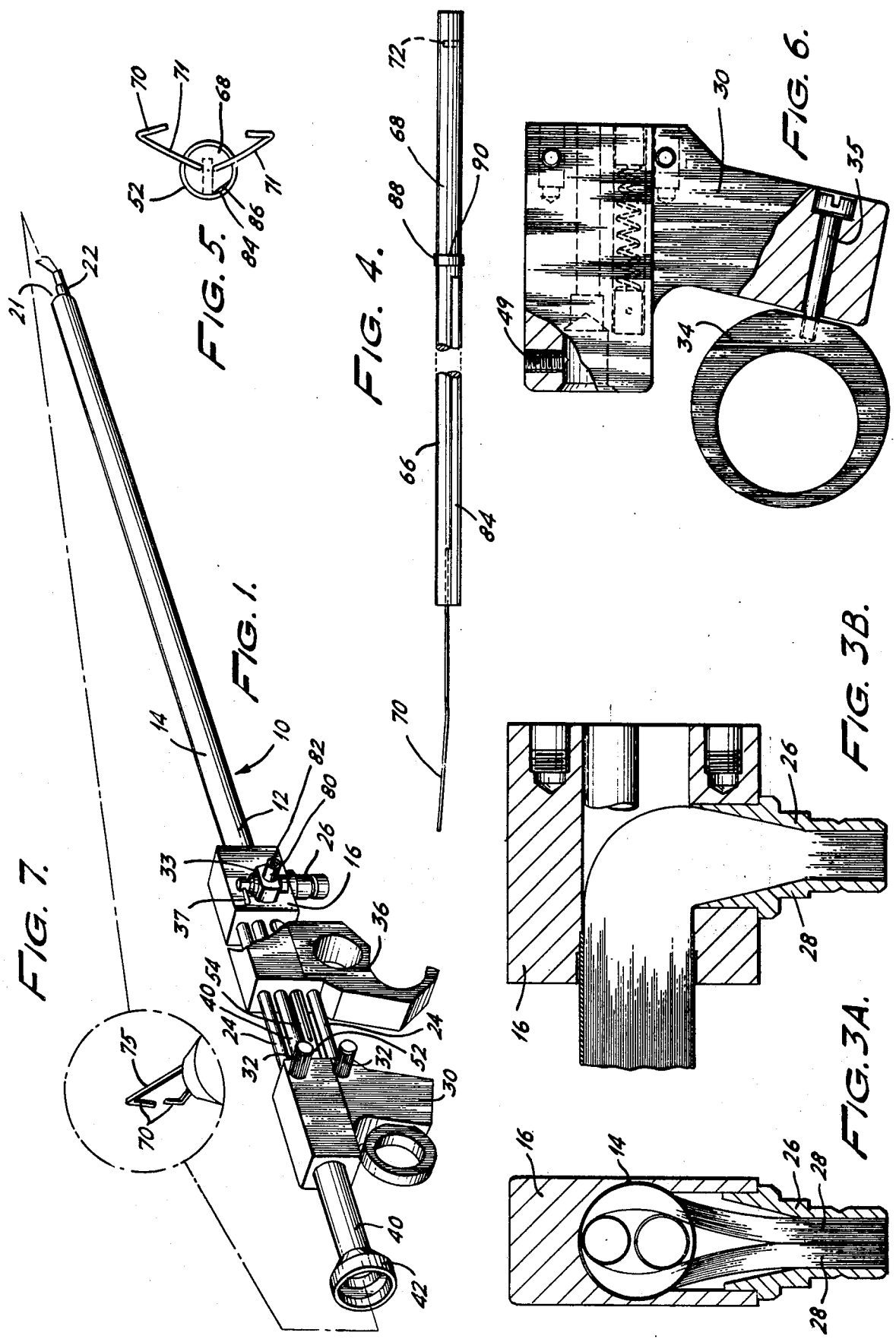

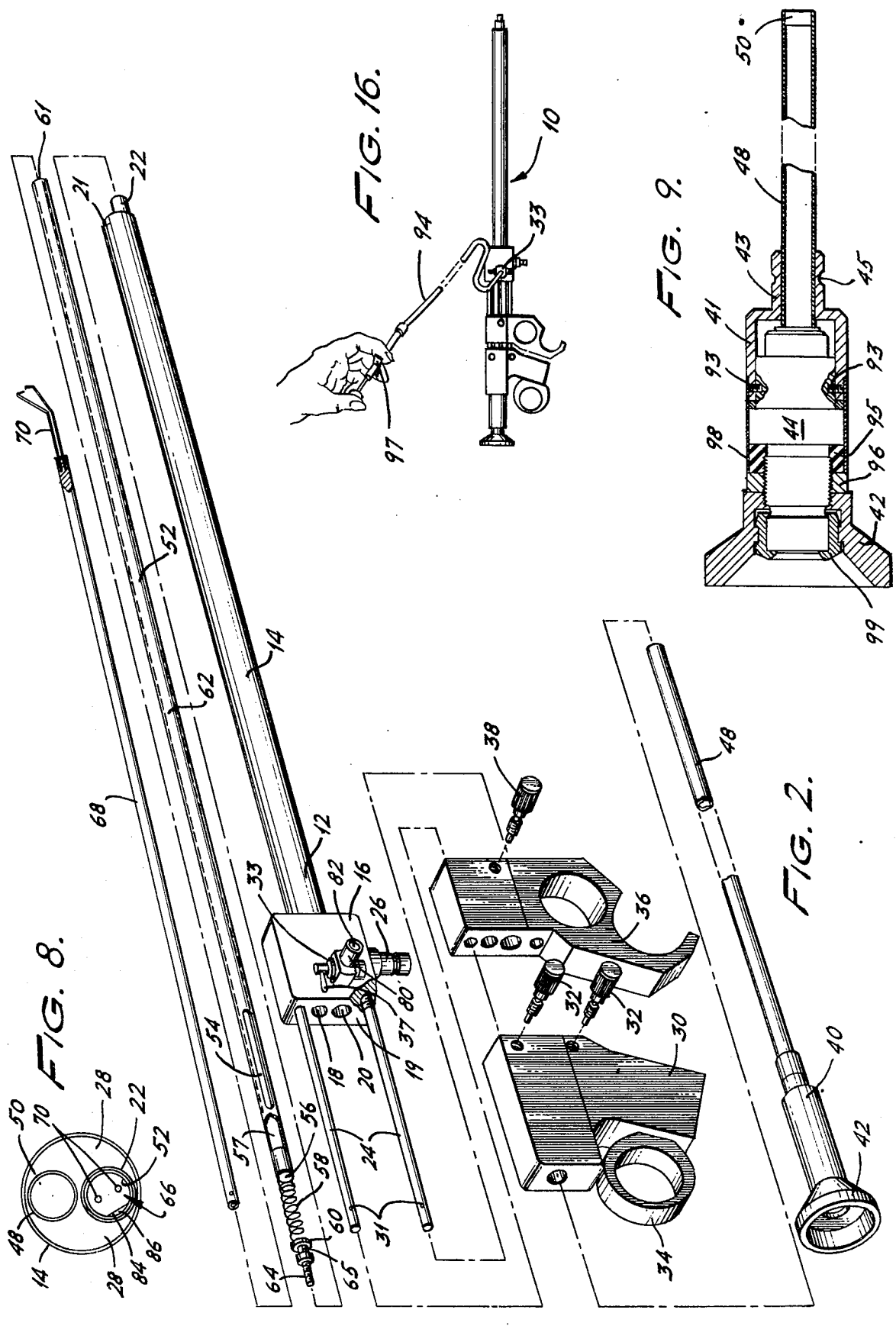

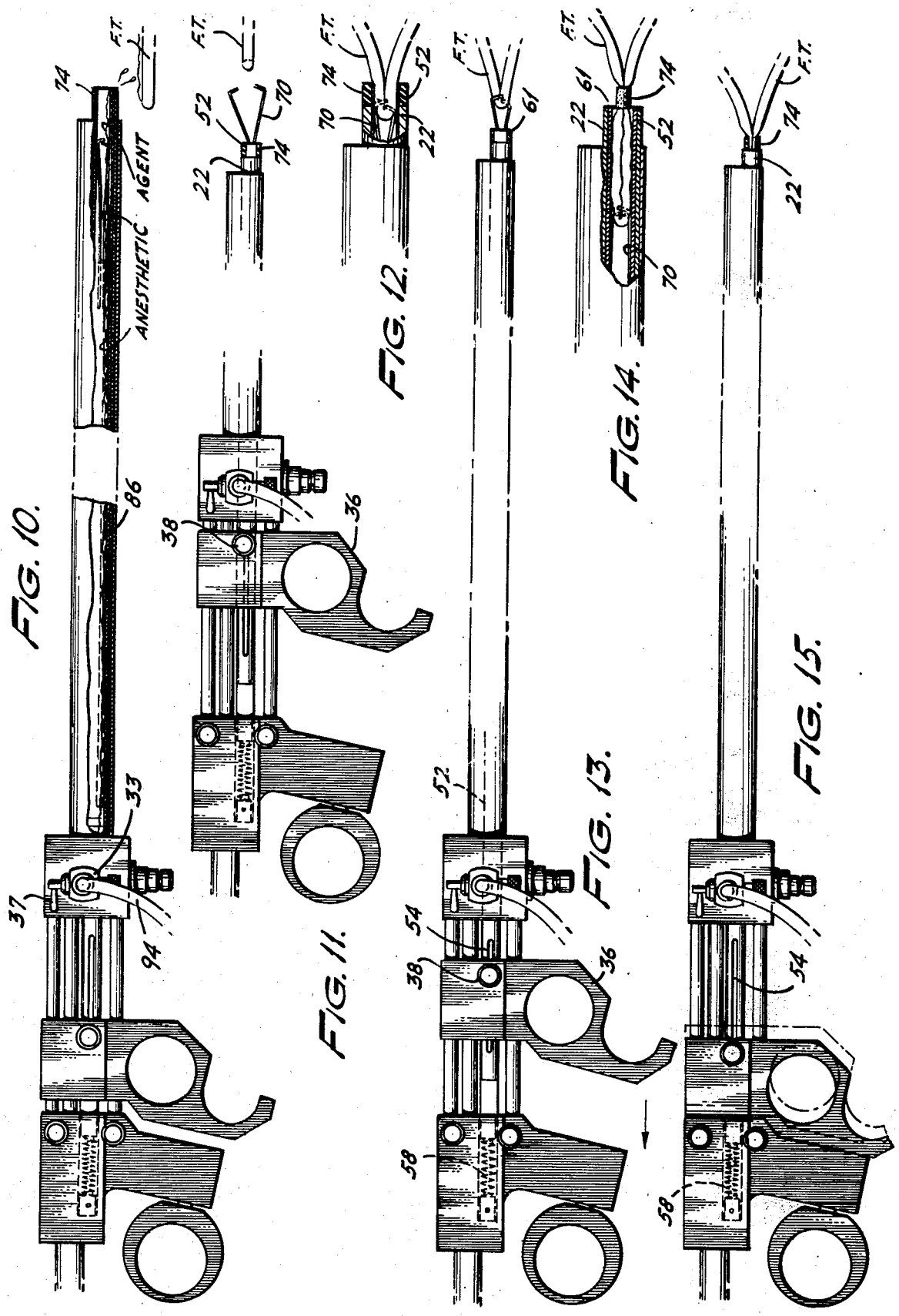

TUBAL LIGATION INSTRUMENT WITH ANESTHESIA MEANS

BACKGROUND OF THE INVENTION

The present invention relates to a tubal ligation instrument for ligating anatomical elements, and more specifically relates to such an instrument which further includes a means for intraabdominally anesthetizing an anatomical element. The present invention also relates to the method of using such a tubal ligation instrument. Although this instrument relates particularly to female sterilization procedures involving the Fallopian tubes, the instrument of this invention may be applied to the vas deferens in the human male and to any other suitable anatomical structure.

Tubal ligation instruments have found worldwide acceptance for a wide variety of purposes, but in particular have been used for sterilization. In the U.S. Pat. No. 3,834,392, granted to Lampman et al. on Sept. 10, 1974, there is disclosed a laparoscope system for sterilization whereby a single unit contains the power source to provide illumination, oscillatory electrical power and $CO_2$ gas for laparosocopy. The $CO_2$ gas, under pressure is first passed into the body through a needle into the peritoneal cavity. A trocar and cannula are inserted into the gas-filled abdominal cavity. A telescope connected to a source of illumination is inserted into the body cavity through the cannula. The Fallopian tubes are then identified through the laparoscope. Flexible forceps are thereafter inserted through the laparoscope into the body cavity. The forceps is manipulated to successively close the passage through each Fallopian tube either by means of sending electrical oscillations through the forceps to simultaneously cut, seal and cauterize each tube in turn, or by means of a specific clamp which clamps the passage shut.

U.S. Pat. No. 3,760,810 to Van Hoorn, granted Sept. 25, 1973 shows a surgical ligation instrument for ligating internal structures of a cavity in the human body, such as internal hermorrhoids, by means of at least one elastic cord. In the Van Hoorn device, two tubes are mounted for relative sliding movement, one inside the other, with the inner tube protruding at the front of the outer tube. An elastic cord or band is stretched upon the outer surface of the protruding portion of the inner tube, and after the tube to be ligated has been drawn into the inner tube, relative movement of the outer tube to the inner tube, displaces the elastic band about the grasped tube. Thus, a stretchable or elastic cord or ring is used for tubal ligation of blood vessels in the treatment of rectosigmoidal lesions and in the treatment of internal structures of the human body.

The preceding patents have been described as showing the present state of the art of tubal ligation instruments. However, in using any of these prior art tubal ligation instruments, there is no teaching of incorporating with the ligation instrument means for locally anesthetizing the anatomical element to be ligated. An object of the tubal ligation instrument of the present invention, and its method of utilization is to allow the surgeon to introduce intraabdominally an anethetic agent to the anatomical element. This anesthesia which is dispensed through the instrument of the present invention may be applied to an anatomical element, for example a Fallopian tube, thus minimizing the pain during and after the ligation procedure. Thus, the ligation instrument with its associate anesthesia dispensing means fulfills a most beneficial need in tubal ligation procedures.

SUMMARY OF THE INVENTION

A tubal ligation instrument includes a housing, an elastic ring supporting means slidable in the housing, and an elastic ring displacement means coaxial with the support means. Means for causing a relative movement of the support means to the displacement means are further provided so that the displacement means causes the displacement of one or more elastic rings off of the support means. The tubal ligation of the present invention further includes the improvement of an anatomical element grasping means slidable in the support means, with a channel between the grasping means and the support means. A means for receiving an anesthesia agent is on the housing of the instrument. The receiving means also has a channel therethrough. The grasping means is further adapted so that the grasping means channel can communicate with the channel of the receiving means so as to introduce an anesthetic agent through the instrument and to an anatomical element during the operation of using the ligation instrument.

BRIEF DESCRIPTION OF THE DRAWINGS

FIG. 1 is a perspective view of the tubal ligation instrument of the present invention.

FIG. 2 is an exploded view of the tubal ligation instrument of FIG. 1.

FIGS. 3a and 3b are respectively front and side cross-sectional view of the fiberoptic bundle in the present invention.

FIG. 4 is a bottom plan view showing a flat surface on the grasping assembly of FIG. 2.

FIG. 5 is a front elevational view of the grasping assembly of FIG. 4 in the inner tube as shown in FIG. 2.

FIG. 6 is a detailed cross-sectional view of the stationary grip means of the present invention.

FIG. 7 is a view of the forceps of the present invention as viewed through optical viewing means of the present invention.

FIG. 8 is a frontal view of the tubal ligation instrument of the present invention as shown in FIG. 1.

FIG. 9 is a cross-sectional view of the optical viewing means of the present invention.

FIGS. 10 to 15 are cross-sectional and side views illustrating the operation of the tubal ligation instrument of the present invention.

FIG. 16 is a perspective view of the ligation instrument of the present invention with means for disposing an anesthetic agent into the ligation instrument.

DETAILED DESCRIPTION OF THE INVENTION

Referring to the Figures, the tubal ligation instrument of the present invention with means for dispensing an anesthetic agent is designated as 10. The ligation instrument 10 includes a housing assembly 12 having an elongated tubular member 14 which is attached at one of its ends to a block member 16. The tubular member 14 has a distal end 21 opposite the end attached to the block member 16. Extending through both the elongated tubular member 14 and the block member 16 are first and second channels 18 and 20. The channels 18 and 20 each have longitudinal axes substantially parallel to each other and each channel is spaced substantially from each other in the transverse direction. Extending from the distal end 21 of elongated tubular member 14 is an elastic ring displacement means 22, which is typically tubular in form and has an opening or channel therethrough, coaxial with the second channel 20 of the tubular member 14. The block member 16 includes a surface 19, which is the surface spaced from the tubular member 14 and through which the first and second channels 18 and 20 form openings therein. Extending from a surface 19 of the block member 16 is a pair of substantially parallel guide means 24, typically in the form of cylindrical rods. The guide rods 24 are shown in FIG. 2 as being screwably mounted into openings in the block member 16. However, the present invention can also be practiced if the rods 24 are permanently fixed to the block member 16.

Extending from a surface of the block member 16, typically a top or bottom surface is a fiberoptic connector 26. The fiberoptic connector 26 is permanently fastened to the block member 16. A bundle of fiberoptics 28 extends through an opening in the fiberoptic connector 26 and into the block member 16 where the bundle 28 is equally divided into two separate bundles which extend through spaces between the first and second channels 18 and 20 in the elongated tubular member 14, to the distal end 21 of the tubular member 14, as shown in FIGS. 3a and 3b. Referring to FIG. 8, the ends of the split-apart fiberoptic bundle 28, are shown as being spaced on either side of the first and second channels 18 and 20. Typically, the ends of the fiberoptic bundle 28 at the fiberoptic connector 26 and at the distal end 21 are typically ground and polished so as to increase light conduction into and out of the fiberoptic bundle 28. As will be most apparent from the following description of the ligation instrument 10, of the present invention, in the operation of the instrument 10, a lighting means (not shown) is attached to the fiberoptic connector 26 and light will travel through the equally-split parts of the fiberoptic bundle 28 to the distal end 21, thereby providing illumination for the ligation procedure.

Attached to a surface of the block member 16, typically a side surface, is a means for receiving an anesthetic agent. For the purpose of describing the present invention, the receiving means will be described as a stopcock 33. Referring to FIG. 2, the stopcock 33 includes a lever arm 37 which operates a conventional valve (not shown) inside of the stopcock 33. Extending from the stopcock 33 is an input tube 80, having a channel 82 which extends through the stopcock 33 and into the block member 16. The lever arm 37 through the valve in the stopcock 33 opens and closes the channel 82 to the flow of an anesthetic agent from an external source. How the stopcock 33 operates with other members of the tubal ligation instrument 10 in anesthetizing anatomical elements will be appreciated more readily from the subsequent discussion of the present invention.

A stationary gripping means 30 is attached to the guide rods 24 at the end of the guide rods opposite the block member 16, by a pair of screws 32. Small holes 31 are formed in the ends of the guide rods 24, which mate with the stationary gripping means 30. These ends of the guide rods 24 fit into openings in the stationary gripping means 30, and the gripping means 30 is then fixed to the guide rods 24 by the two screws 32. The screws 32 are shown in more detail in FIG. 2. The screws 32 have a large diameter portion at one end which is knurled and easily grasped with the fingers, a smaller-diameter threaded section, and a still smaller-diameter unthreaded or pin section at an opposite end.

The threaded portion of the screws 32 is screwed into the gripping means 30 and the pin section of the screws 32 mate with the holes in the ends of the guide rods 24, thereby securing the stationary gripping means 30 to the guide rods 24.

A first channel extends completely through the stationary gripping means 30 and is in substantial alignment with the first channel 18 through the housing assembly 12. Furthermore, a second channel extends at least partially through the stationary gripping means 30 and is in substantial alignment with the second channel 20 of the housing assembly 12.

The stationary gripping means 30 is shown in the drawings as having a shape substantially that of a pistol grip. However, of most importance is the thumb-gripping means 34 at the lower portion of the stationary gripping means 30. The thumb-gripping means 34 is rotatable on the gripping means 30 and attached thereto by a screw 35, as shown in FIG. 6. The screw 36 is unthreaded in the gripping means 30 and is only screwed to the thumb-gripping means 34, thus it is rotatable. The rotatable thumb-gripping means 34 provides a comfortable means of grasping the instrument 10, whether the surgeon be left - or right-handed. Since the thumb-gripping means 34 is rotatable, it can move about to fit comfortably on either a right-handed or left-handed thumb. While the stationary gripping means 30 and the thumb-gripping means 34 are shown as being in a piston-grip shape and annular in shape respectively, it should, nevertheless, be appreciated that the gripping means 30 and thumb-gripping means 34 can have other conventional shapes which make possible the practice of the ligation instrument 10 of the present invention. For example, the thumb-gripping means 34 can be of a generally U-shape or generally square shape.

A slidable gripping means 36 has openings therethrough so that it can slide along the guide rods 24 between the block member 16 and the stationary gripping means 30. Also extending through the slidable gripping means 36 is a first and second channel in substantial alignment with the first and second channels of the housing assembly 12 and stationary gripping means 30. The slidable gripping means 36 is typically grasped by at least some of the fingers of either the right or left hand. Thus, it is shown in the Figures as having a large hole therethrough for grasping by at least one finger, and in addition has a hook-shaped or trigger portion for gripping by one or more additional fingers. The shape of the slidable gripping means 36 as described is by way of example, since other conventional shapes can be utilized in the practice of the present invention. A screw 38, similar to the screws 32, extends from a side of the slidable gripping means 36. The purpose of the screw 38 will be more apparent from the subsequent description of the present invention.

An optical viewing means 40 slides through the first channels of the stationary gripping means 30, the slidable gripping means 36 and the housing assembly 12. The optical viewing means 40 is typically in the form of an endoscope. The endoscope 40 is slidable in the ligation instrument 10 and also locks into the ligation instrument 10.

Referring to FIG. 9, the endoscope 40 comprises a body 41, substantially tubular in shape, with a neck member, designated as 43, fixed to and extending from one end of body 41. An eyepiece assembly 44, containing eyepiece lenses therein and having a threaded end, is mounted within the body 41 by set screws 93, so that the threaded end is spaced opposite from the neck member 43.

The threaded end of eyepiece assembly 44 mates with an eyeshield 42 of an electrically nonconducting material. However, prior to screwing eyeshield 42 onto the eyepeice assembly 44, a cover ring 98 is slid over the body 41 covering set screws 93, a water proof sealing compound 95 is disposed between the cover ring 98 and eyepiece assembly 44, and then a lock ring 96 is secured onto the threaded end of eyepiece assembly 44 for retention of the cover ring 95.

An annular shaped grommet 99 is mounted into the opening of the eyeshield 42. Grommet 99 is of an electrically nonconducting material, and prevents the surgeon's eye from contacting the metal of the eyepiece assembly 44. Bonded to the neck member 43 of the body 41 is an elongated tubular member 48 which contains therein an objective assembly and a train of relay lenses (not shown). A window lens 50 is sealed, with a water proof sealer, into the distal end of the tubular member 48.

One of the major advantages of the present invention is that the endoscope 40 can be easily slid into and out of the ligation instrument 10 for cleaning, maintenance, sterilization or replacement.

As previously stated, the endoscope 40 is also lockable in the ligation instrument 10. A groove 45 extends into and around the outside surface of the neck member 43. The first channel 18 in the stationary gripping means 30 is enlarged at the rearward portion of the stationary gripping means 30 to mate with the neck member 43. Also in the stationary gripping means 30 is a locking device which in the present instance is a ball plunger 49 which mates with the groove 45 as shown in FIG. 6. It is the combination of the ball plunger 49 and groove 45 which provides the locking mechanism for the endoscope 40. This locking mechanism prevents the endoscope 40 from inadvertently falling out of the instrument 10. The endoscope 40 is put into and taken out of its locked position by the application of a force in the forward and rearward longitudinal directions of the endoscope 40 respectively.

The slidable endoscope 40 mates into the housing 12 so that the distal end of the longitudinal tubular member 48 is substantially flush with the distal end 21 of the tubular member 14 of the housing 12. This placement of the distal end of the endoscope 40 is quite important since it is beneficial in preventing the accidental chipping of the window lens 50 onto hard objects. Furthermore, the distal end of the tubular portion 48 of endoscope 40 is spaced behind that portion of the instrument 10 from which elastic rings are displaced during the ligation procedure (as will be evident from the forthcoming explanation of the operation of the present invention). Thus, there is less likelihood that the grasping of the ligated anatomical element will interfer with or accidentally block the viewing of the ligation procedure, because of the ungrasped portion of the anatomical element falling in front the window lens 50. Furthermore, the endoscope 40 and the window lens 50 are transversely spaced from the means for displacing the elastic rings onto the anatomical elements, i.e., the inner tube 52 and displacement means 22, thereby providing good visibility of the ligation procedure.

Referring to the Figures and particularly to FIG. 2, an inner tube 52 is slidable through the second channel of the slidable gripping means 36 and the housing assembly 12. The inner tube member 52 has a slot 54 which extends longitudinally along a portion of the inner tube 52; the purpose for the slot 54 will be more readily understood from the subsequent description of the present invention. The inner tube member 52 has a distal end 61. At an opposite end of the inner tube 52, is a slug 57 fixed therein. Extending from this opposite end is a collar 56. Bonded to the collar 56 is a biasing means 58 which is typically a helical compression spring. The spring 58 is typically bonded to the collar 56 of the inner tube 52 by soldering. The spring 58 has approximately the same outer diameter as the inner tube 52. Attached to the opposite end of the spring 58 as a threaded element 60 which has a collar 65 to which the spring 58 is bonded with threaded portion 64 extending therefrom. The inner tube 52 and spring 58 are mounted to the ligation instrument 10 by screwing the threaded element 60 into a threaded opening of the stationary gripping means 30, which threaded opening is in substantial alignment with the second channel in the slidable gripping means 36 and the housing assembly 12. For the purpose of describing the present invention, the inner tube 52 with the spring 58 and threaded element 60 are hereinafter described as the inner tubular assembly 62. The inner tubular assembly 62 is mounted into the ligation instrument 10 so that the slot 54 extends substantially between the stationary gripping means 30 and the block member 16, and also so that the distal end 61 of the inner tube member 52 extends beyond the elastic ring displacement means 22. As will be readily understood from the subsequent explanation of the operation of the present invention, the portion of the inner tube 52 at the distal end 61 is adapted for supporting one or more elastic rings used for ligating anatomical elements.

Slidable in the inner tube 52 is a grasping assembly 66 having an elongated rod member 68 that has a grasping means 70, such as forceps tongs attached at the forward end of the rod member 68. The forceps tongs 70 are designed to grasp an anatomical element to be ligated, such as a Fallopian tube in a female or a vas deferens in a male. The rod member 68 has a flat surface 84 which extends from the forward end of rod member 68 along a portion of the rod member 68, reference FIGS. 4 and 5. Thus, a portion of the rod member 68 toward the rear end has a substantially circular cross-sectional form, while the forward end of the rod 68 has a cross-sectional form typically somewhere between a circle and a semicircle. The inner tube fits slidably over rod member 68 so that a channel 86 is formed between the flat surface 84 and the inner tube 52, as shown in FIGS. 5 and 10. A washer means 88, typically a ring of polytetrafluoroethylene, also known as PTFE, is placed in a groove 90 which is formed in the rearward portion of rod 68 at a position slightly rearward of that point where the flat surface 84 ends. Since the rearward portion of the rod member 68 is circular in its cross section and has an outside diameter only slightly smaller than the inside diameter of the inner tube 52, and because a seal is formed between the ring 88 and the inner surface of inner tube 52, any gas, which has been pumped into the body cavity in the course of the ligating procedure, cannot escape in any significant amounts between these two elongated members.

The elongated rod member 68 has a hole 72 that extends through the diameter of the rod member 68 near the end of the rod 68 opposite the grasping means 70. The grasping assembly 66 is positioned in the inner tube 52, so that the hole 72 is in alignment with the slot 54. The pin portion of the screw 38, which has been screwed into slidable gripping means 36, extends through the slot 54 and mates with the hole 72. Thus, the forward and rearward slidable movement of the gripping means 36 consequently moves the grasping assembly 66 along the inner tube member 52.

At some position in retracting the grasping assembly 66 by the rearward movement of the slidable gripping means 36, the channel 86 (between the flat surface 84 and inner tube 52) communicates with the channel 82 of the stopcock 33. This position is typically just prior to the slidable gripping means 36 encountering the resistance of the spring 58. The surgeon feels this resistance in the slidable gripping means 36. More specifically, this position is encountered when the end of the channel 86 and the ring 88 are positioned slightly behind the channel 82 of the stopcock 33. Generally the end of the channel 86 is positioned about 0.125 inch behind the stopcock channel 82 when the grasping assembly means 66 is retracted just prior to encountering the resistance of spring 58. Thus, it is readily apparent from the previous description of the stopcock 33 and the grasping assembly 66 and its means of operation, that when the slidable gripping means 36 retracts the grasping means 66 to that position where the channel 86 is in communication with channel 82, an anesthetic agent can flow through the channel 82 of the stopcock 33, and into the channel 86 and along the inner tube 52 to the distal end 61. The distal end 61 of inner tube 52 is directed toward and is in close proximity with, if not touching, an anatomical element. The anesthesia agent flows onto the anatomical element thereby anesthetizing it.

The ring 88 which is located immediately behind the flat surface 84 on the rod member 66, functions as a seal to prevent the leakage of any anesthesia agent towards the rearward position of the instrument 10. When the anesthesia channels 86 and 82 are not being used, the stopcock 33 is in the closed position by the operation of the lever arm 37.

The forceps tongs 70 has leg portions 71 which are spring-like in nature so that the leg portions 71 spread apart when the forward movement of the slidable gripping means 36 positions them beyond the distal end 61 of the inner tube 52. When the forceps tongs 70 are in the open position, beyond the distal end 61, they are preferably angled in an upward direction and further angled either to the right or to the left so that they are more readily viewed through the endoscope 40, i.e., more or less in front of the window lens 50. It must be remembered that the end of the endoscope 40, i.e., window lens 50, is positioned slightly above the distal end 61 of the inner tube 52. Thus, by angling the forceps tongs 70 as described, there is a substantial improvement in the view afforded the surgeon during the ligation procedure. FIG. 7 shows the excellent view of the ligation process afforded to the surgeon by having the forceps tongs 70 angled as described above.

Retracting the forceps tongs 70 back into the inner tube 52, by the rearward movement of the gripping means 36, closes the spring-like leg portions 71 of the forceps tongs 70. It is preferable that in the closed position leg portions 71 of the forceps tongs 70 be staggered slightly with respect to one another, and pass closely adjacent to each other when they are in the closed position.

The slidable motion of the gripping means 36 moves the forceps tongs into and out of the inner tube 52. A portion of the inward and outward movement of the forceps tongs 70 occurs while the pin portion of the screw 38 is sliding freely through the slot 54 of the inner tube 52. When the gripping means 36 is slid rearwardly so that the rear end of the rod member 68 pushes upon and contacts the slug 57 in the end position of the inner tube 52, the rearward movement of the grasping assembly 66 continues. However, the gripping means 36 as a result of this encounter will also slide the inner tube 52 in the rearward direction against the compressional force of the biasing means 58. This position was described previously in the discussion of the application of an anesthesia agent to an anatomical element.

When the biasing means 58 is fully extended, the distal end 61 of the inner tube 52 extends beyond the displacement means 22. Thus, it should be readily apparent from the preceding description of the ligation instrument 10, that once an anatomical element has been grasped by the forceps tongs 70 and withdrawn into the inner tube 52 by the rearward movement of the gripping means 36 further rearward movement causes the engagement of the rear end of the rod 68 with slug 57. Consequently, this further rearward movement causes the distal end 61 of the inner tube 52 to retract within the elastic ring displacement means 22. This relative movement between the distal end 61 and displacement means 22 causes the displacement of elastic rings off the distal end 61 and onto the folded-over crimped anatomical element for ligation thereof. When the biasing means 58 is fully compresse;d, the distal end 61 is substantially within the displacement means 22.

Referring to FIG. 8, the forward end of the present invention is shown. In this particular example of the present invention, the window lens 50 is above the means for displacing the elastic rings, i.e., the displacement means 22 and the inner tube 52, as well as the grasping assembly 66. Furthermore, the two separate portions of the fiberoptic bundle 28 are shown as terminating on the front face of the instrument 10. While this is a preferred arrangement, it is also anticipated by the present invention that the equally parted portion of fiberoptic bundle 28 may be arranged in a different manner or can be divided into more portions as long as sufficient light is provided for viewing the subject ligation procedure. Furthermore, from FIG. 8, the channel 86, through which the anesthetic agent flows to the anatomical element, is quite apparent.

The operation of the ligation instrument 10 of the present invention is subsequently described in more detail. In order to better describe the operation of the ligating instrument 10, reference will be made to its use in anesthetizing and occlusion of the Fallopian tubes of a female patient, referring to FIGS. 10 to 16. It should be remembered that such reference is for illustrative purposes only, as the novel apparatus of the present invention may be utilized to anesthetize and ligate any anatomical tubular structures. Therefore, description of the operation aspects of the invention should be construed as being descriptive only, and not limiting in any manner whatsoever. In referring to the sequence of steps performed, FIGS. 10 to 16 may be considered as illustrative of typical steps as performed by the surgeon in anesthetizing and ligating a Fallopian tube.

Referring to FIG. 16, a flexible tube 94 is attached to the input tube 80 of the stopcock 33. Typically, the flexible tube 94 is a conventional intravenous tube. Attached to the opposite end of the flexible tube 94 is an anesthesia dispensing means 97 typically a syringe. The syringe 97 contains a local anesthetic agent which is to be used in the anesthetizing procedure. The anesthetic agent will usually be in a liquid form and is a conventional local anesthesia such as that known by the trade name Bupivicaine. The conventional anesthesia is usually transparent, thus a dye agent is usually added to the anesthesia so that the surgeon can more readily view the anesthesia being dispensed onto the anatomical element to be ligated.

Typically, prior to utilizing the instrument 10 of the present invention, the instrument must be purged. This purging procedure requires the retraction of the slidable gripping means 36 to that position just before it encounters resistance from the spring 58. Thereupon, the plunger of the syringe 97 is pushed until an even flow of liquid anesthesia is observed at the distal end 61 of the inner tube 52. The stopcock 33 is then closed by actuating the lever arm 37.

An elastic ring 74 is loaded onto the distal end 61 of the inner tube 52 by conventional means. It should be understood that the length of the distal end portion of the inner tube 52 protrudes from the displacement means 22 a distance equal to at least N×W (wherein N is equal to the number of elastic rings to be loaded about the distal end portion, and W is equal to the width of the elastic rings).

Referring to FIG. 10, after suitable incision, insufflation of the anatomical cavity (if applicable) and insertion of the instrument, the surgeon again retracts the slidable gripping means 36 to that position prior to encountering the resistance the spring 58, i.e. when the channel 86 is in communication with the channel 82. Again the stopcock 33 is opened by operation of the lever arm 37. At this time the distal end 61 of the inner tube 52 is directed towards and in close proximity with, if not touching, the anatomical element to be ligated. The plunger of the syringe 97 is then pushed, forcing the anesthesia agent with a dye through the flexible tube 94 into the channels 82 and 86 and along the inner tube 52 to the distal end 61 where upon the anesthesia is dispensed onto the Fallopian tube. The Fallopian tube is thereby anesthetized and the stopcock closed by actuation of the lever arm 37.

As previously stated, since the anesthesia agent includes a dye, the surgeon can readily view its contacting the Fallopian tube. The surgeon then displaces the slidable gripping means 36 in a forward direction, causing the forceps tongs 70 to protrude forward of the distal end 61 and assume its opened position. The grasping assembly 66 is caused to move forwardly as shown in FIG. 11, with respect to both the inner tube 52 and displacement ring 22, due to the engagement of the pin portion of screw 38, carried by the slidable gripping means 36, in opening 72 of the rod member 68, as previously described in connection with FIG. 2.

As shown in FIG. 11, the forceps tongs 70, being made of a spring-bias metal, open automatically upon forward displacement from the confines of the inner tube 52. When a Fallopian tube (F.T.) has been grasped, as shown in FIG. 12, the surgeon slowly pulls the slidable gripping means 36, as indicated by the arrow in FIG. 13. As a result of the engagement of the pin portion of screw 38 into the opening 72, the forceps tongs 70 is rearwardly withdrawn inside inner tube 52 by the rearward movement of slidable gripping means 36, as shown in FIG. 13. Since the Fallopian tube has been anesthetized, its being grasped and its later ligation is not painful to the patient.

No resistance is encountered by the spring 58 during the rearward movement of the grasping assembly 66 and the grasped Fallopian tube until the rear end of rod 68 pushes upon and contacting the slug 57. Further rearward movement of the slidable gripping means 36, after such contact, is resisted by spring 58. Also, such further retraction of the slidable gripping means 36 causes the displacement of inner tube 52. Specifically, distal end 61 moves rearwardly relative to the elastic ring displacement means 22. This further retraction therefore displaces the elastic ring 74 forward of the distal end 61, ultimately ejecting the elastic ring 74 onto the doubled-over anesthetized Fallopian tube, referring to FIGS. 14 and 15.

The surgeon, upon encountering the resistance due to the spring 58, knows that the elastic ring is about to be ejected from the distal end 61 of the inner tube 52.

Without withdrawing the ligation instrument 10 from the body cavity, the surgeon pushes the slidable gripping means 36 forwardly, to expel the now-occluded Fallopian tube from the inner tube 52, thus causing the forceps tongs 70 to move in the forward direction, until they are free to spring open to release the Fallopian tube. The spring 58 urges the inner tube 52 forward during the first pair of this forward movement without the additional help form the surgeon's fingers.

By repeating the procedure as described above, the second Fallopian tube is also anesthetized and ligated. Upon completion of the steps described, both Fallopian tubes are occluded and the operation may be completed by withdrawing the ligation instrument 10 and closing the incision.

It must be remembered that during the ligation procedure the surgeon is viewing the procedure through the endoscope 40, and that the fiberoptic bundle 28 is transmitting light to the area of the body cavity on which the procedure is being performed. As a result of the angled forceps 70, the ligation procedure is readily viewed by the surgeon as he looks through the eyeshield 42 of the endoscope 40. Furthermore, the rotatable thumb-gripping means 34 has made the handling of the instrument most comfortable to either a right-handed or left-handed physician.

While the channel 86 has been described as being formed because the grasping assembly 66 has machined thereon a flat surface 84, it is nevertheless anticipated by the present invention that the surface 84 may not be flat but could be of another conventional shape which would provide the necessary channel. For example, the surface 84 could be somewhat concaved in its configuration.

The ligation instrument of the present invention is very easy to disassemble, clean, sterilize, and reassemble. As viewed in FIG. 2, the separate parts contain mostly open and easily-accessible surfaces. Of most importance is the fact that the laparoscope 40 is easily withdrawn from the first channels in the body assembly 12, gripping means 36, and stationary gripping means 30. Although it is preferred to clean and sterilize the parts separately, they can be cleaned separately, and then reassembled and sterilized as one unit.

In disassembling the ligation instrument 10, the viewing means 40 is gently disengaged from the instrument 10 by holding the slidable gripping means 36 in one hand and pulling the viewing means 40 with the other. The forceps 70 are extended forward by moving the slidable gripping means 36 to its forwardmost position, and then the screw 38 is removed by turning it in a counter clockwise direction. Then holding the instrument 10 with one hand, the other hand is used to gently pull the forceps 70 and the grasping assembly 66 completely out of the inner tube 52. Holding the stationary means 30 with one hand, the other hand is used to unscrew the inner tube assembly 52 from the stationary gripping means 30. Unscrewing the inner tube assembly 62 is most easily accomplished by grasping the fluted portion of the inner tube 52 which is rearward of the slot 56. Then, remove the tubular assembly 62 from the instrument 10. Next, the two screws 32 are removed from the stationary gripping means 30. The stationary gripping means 30 and slidable gripping means 36 are then slid off of the guide rods 24. This completes the disassembly of the ligation instrument 10.

It is highly recommended that the ligation instrument 10 be cleaned immediately after use. This is done by placing the disassembled instrument parts and a cleaning brush in warm water with a mild, not abrasive detergent. A brush may be utilized to clean the insides of the tubular members and it is preferably pushed into the tubes using a rotating motion. After cleaning, the outside of the tube members are easily wiped off with a soft cloth and the parts are rinsed thoroughly with clean water and the excess liquid is shaken off, then all parts are air-dried.

The provision of the spring 58, or any other equivalent resistance device such as an air or gas cylinder, bellows or the like, is important in that it assures the surgeon that the ligation instrument cannot discharge the elastic ring prematurely. It is normal in the operation of the ligating instrument 10 for the surgeon to feel the increased resistance, due to the spring 58, at the time that the forceps 70 have been completely withdrawn within the inner tube 52, and the surgeon must deliberately draw the slidable gripping means 36 rearwardly against the resistance in order to cause the release of the elastic ring.

Of most importance, the tubal ligation instrument of the present invention includes means for anesthetizing the present invention includes means for anesthetizing an anatomical element which is to be ligated. Now as a consequence of the present invention, a surgeon can use one instrument to both intraabdominally anesthetize anatomical structure and ligate the same anatomical element.

Although this instrument has been described in connection with specific forms thereof, it will be appreciated by one reading the preceding description of the present invention that a wide variety of equivalents may be substituted for those specific elements and steps of operation shown and described herein, that certain features may be used independently of other features, all without departing from the spirit and scope of this invention as defined in the appended claims.

I claim:

1. In a tubal ligation instrument of the type having a housing, an elastic ring support means carried by said housing, an elastic ring displacement means, a means for causing a relative movement of said support means to said displacement means for displacing an elastic ring off of said support means in a manner to perform a tubal ligation, the improvement which comprises:
   (a) an anatomical element grasping means slidable in said support means, with a channel between said grasping means and said support means;
   (b) a means for receiving an anesthetic agent on said housing, said receiving means having a channel therethrough, said grasping means adapted so that said channel between said grasping means and said support means communicates with the channel of said receiving means so as to introduce an anesthetic agent to a grasped anatomical element;
   (c) actuating means for reciprocally sliding said grasping means axially along said support means, said receiving means communicating with said channel between said grasping means and said support means during only a portion of said reciprocal sliding motion.

2. The tubal ligation instrument in accordance with claim 1, wherein said anatomical element grasping means comprises an elongated rod member having a flat surface along a portion thereof so as to form said channel between said support means and said grasping means.

3. The tubal ligation instrument in accordance with claim 2, wherein said flat surface extends from a distal end of said rod member which is adapted to grasp an anatomical element and extends therefrom along a portion of said rod member to a point at which said flat surface ends.

4. The tubal ligation instrument in accordance with claim 3, further comprising a washer means surrounding said rod member and positioned in close proximity to said point on the rod member at which the flat surface ends.

5. The tubal ligation instrument in accordance with claim 4, wherein said washer means is a ring of polytetrafluroethylene.

6. The tubal ligation instrument in accordance with claim 2, wherein said grasping means further comprises at an end of said rod member, forceps tongs having a pair of spring-like legs adapted for grasping said anatomical element to be ligated.

7. The tubal ligation instrument in accordance with claim 1, wherein said anesthesia receiving means is a stopcock having an input tube with a channel therethrough and a lever operating a valve for opening and closing said channel.

8. The tubal ligation instrument in accordance with claim 7, further comprising a flexible tube attached to said input tube of said stopcock and an anesthetic agent dispensing means attached to the other end of said flexible tube.

9. The tubal ligation instrument in accordance with claim 8, wherein said anesthetic agent dispensing means is a syringe.

10. The tubal ligation instrument in accordance with claim 1, further comprising resistance means operatively associated with said actuation means for providing a manually detectable increase in resistance in said portion of said reciprocal sliding when said channel between said grasping means and said support means is in communication with said receiving means channel.

11. The tubal ligation instrument in accordance with claim 1, further comprising an optical viewing means slidable in said housing and having a longitudinal axis substantially parallel to and spaced transversely from said support means, said optical view means adapted for viewing the ligation of an anatomical element.

12. The tubal ligation instrument in accordance with claim 11, wherein said viewing means is an endoscope.

13. A tubal ligation instrument for displacing at least one elastic ring onto an anatomical element or elements and for anesthetizing said element or elements comprising:
   a housing;
   an elastic ring support means having a portion thereof adapted for supporting one or more elastic rings thereon, said support means being slidable in said housing;

an elastic ring displacement means attached to said housing, said support means being slidable in said displacement means, said elastic ring support portion of said support means adapted for extending beyond said displacement means;

a means for causing a relative movement of said support means to said displacement means for displacing one or more elastic rings off of said support means;

an anatomical element grasping assembly slidable in said support means;

a portion of said grasping means not occupying said support means so that a channel is formed between said grasping means and said support means;

a means for receiving an anesthetic agent positioned on a surface of said housing, said anesthetic receiving means having a channel therethrough, said grasping means and said anesthetic receiving means being adapted so that said anesthetic receiving means channel communicates with the channel between said grasping means and said support means, so that an anesthetic agent may be introduced through both of said channels to anesthetize an anatomical element, actuating means for reciprocally sliding said grasping means axially along said support means, said receiving means communicating with said channel between said grasping means and said support means during only a portion of said reciprocal sliding motion.

14. The tubal ligation instrument in accordance with claim 13, wherein said grasping means further comprises a rod having a pair of spring-like forceps legs at one end, with a flat surface extending from said forceps end of said rod member along a portion of said rod member to thereby form said channel between said grasping means and said support means.

15. The tubal ligation instrument in accordance with claim 13, wherein said anatomical element grasping means includes a rod member having a pair of spring-like forceps legs for grasping an anatomical element extending from one end of said rod member, a portion of said rod member extending from said forceps end having a cross-section having a shape equal to or greater than a semi-circle but less than that of a full circle.

16. The tubal ligation instrument in accordance with claim 13, wherein said anesthetic receiving means is a stopcock having an input tube with a channel therethrough, said channel being adapted to communicate with said channel between said grasping means and said support means during only a portion of said reciprocal sliding motion of said grasping means, and said stopcock having means to open and close said input tube channel.

17. The tubal ligation instrument in accordance with claim 16, wherein said means for opening and closing said stopcock comprises a lever which operates a valve which in turns opens or closes said input tube channel.

* * * * *